United States Patent
Sharvit et al.

(10) Patent No.: US 9,415,161 B2
(45) Date of Patent: Aug. 16, 2016

(54) APPARATUS, SYSTEM AND METHOD FOR ADMINISTRATION OF A SUBSTANCE

(71) Applicant: PRO-IV LTD., Kfar Vitkin (IL)

(72) Inventors: Pierre Sharvit, Emeq Hefer (IL); Michal Devir, Kfar Vitkin (IL); Jacob Nushbacher, Ra'anana (IL); Gershon Goldenberg, Carcur (IL); Youval Katzman, Zichron Yaakov (IL)

(73) Assignee: PRO-IV Ltd., Kfar Vitkin (IL)

( * ) Notice: Subject to any disclaimer, the term of this patent is extended or adjusted under 35 U.S.C. 154(b) by 642 days.

(21) Appl. No.: 13/771,463

(22) Filed: Feb. 20, 2013

(65) Prior Publication Data

US 2013/0197469 A1  Aug. 1, 2013

Related U.S. Application Data

(63) Continuation-in-part of application No. 11/664,111, filed as application No. PCT/IL2005/001118 on Oct. 26, 2005, now Pat. No. 8,529,552.

(60) Provisional application No. 60/621,659, filed on Oct. 26, 2004.

(51) Int. Cl.
*A61M 5/172* (2006.01)
*A61M 1/02* (2006.01)
(Continued)

(52) U.S. Cl.
CPC ............... *A61M 5/172* (2013.01); *A61M 1/02* (2013.01); *A61M 5/162* (2013.01); *A61M 39/22* (2013.01);
(Continued)

(58) Field of Classification Search
CPC ....... A61M 5/172; A61M 1/02; A61M 5/162; A61M 39/22; A61M 2205/6009; A61M 2205/6072; G06F 19/3468; G06Q 10/00; G06Q 50/24; A61J 1/1487; A61J 2205/10; A61J 2205/60; A61B 5/117; A61B 5/7495
USPC ......................... 604/65–67, 131, 890.1, 151; 128/DIG. 12, 13
See application file for complete search history.

(56) References Cited

U.S. PATENT DOCUMENTS 3,604,419 A * 9/1971 Diskin et al. .................... 604/31
5,154,704 A * 10/1992 Archibald ..................... 604/250
(Continued)

FOREIGN PATENT DOCUMENTS

JP    2003-225305    8/2003
WO    99/10029       3/1999
(Continued)

OTHER PUBLICATIONS

Kaushal R, Bates DW, Landrigan C, et al. Medication errors and adverse drug events in pediatric inpatients. JAMA 285:2114-2120, 2001.

(Continued)

*Primary Examiner* — Manuel Mendez
(74) *Attorney, Agent, or Firm* — Roach Brown McCarthy & Gruber, P.C.; Kevin D. McCarthy

(57) ABSTRACT

The present disclosure relates to an infusion control valve adapted to be actuated by a valve actuator. The present disclosure further relates to an infusion valve actuator adapted to actuate an infusion control valve upon being triggered by an authentication unit. Furthermore, the present disclosure relates to methods for the administration of a substance.

32 Claims, 21 Drawing Sheets

(51) Int. Cl.
*A61M 5/162* (2006.01)
*A61M 39/22* (2006.01)
*G06F 19/00* (2011.01)
*G06Q 50/24* (2012.01)
*G06Q 10/00* (2012.01)
*A61B 5/117* (2016.01)
*A61B 5/00* (2006.01)

(52) U.S. Cl.
CPC ............ *G06F 19/3468* (2013.01); *G06Q 10/00* (2013.01); *G06Q 50/24* (2013.01); *A61B 5/117* (2013.01); *A61B 5/7495* (2013.01); *A61J 1/1487* (2015.05); *A61J 2205/10* (2013.01); *A61J 2205/60* (2013.01); *A61M 2205/6009* (2013.01); *A61M 2205/6072* (2013.01)

(56) References Cited

U.S. PATENT DOCUMENTS

| | | | |
|---|---|---|---|
| 5,433,710 | A | 7/1995 | Van Antwerp |
| 6,519,569 | B1 | 2/2003 | White |
| 6,880,564 | B2 | 4/2005 | Erickson |
| 7,111,817 | B2 * | 9/2006 | Teti et al. .................. 251/129.04 |
| 7,933,780 | B2 | 4/2011 | De La Huerga |
| 2002/0038392 | A1 | 3/2002 | De La Huerga |
| 2004/0171983 | A1 * | 9/2004 | Sparks et al. .................. 604/65 |
| 2008/0287889 | A1 | 11/2008 | Sharvit |

FOREIGN PATENT DOCUMENTS

| | | |
|---|---|---|
| WO | 00/03344 | 1/2000 |
| WO | 00/27275 | 5/2000 |
| WO | 2004/088567 | 10/2004 |

OTHER PUBLICATIONS

Linden JV, Wagner K, Voytovich AE, Sheehan J, Transfusion errors in New York State: an analysis of 10 years' experience. Transfusion 40:1207-1213, 2000 abstract.
Sazama K. Reports of 355 transfusion-associated deaths 1976-1985. Transfusion 30:583-590, 1990.
Taxis K, Barber N. Ethnographic study of incidence and severity of intravenous drug errors. Brit J Med 326:684, 2003.
The Serious Hazards of Transfusion (SHOT) study, Serious Hazards of Transfusion (SHOT), Annual Report, 2003 (6 pages).
To Err is Human: Building a Safer Health System by Kohn LT, Corrigan JM, Donaldson MS, eds. Errors in Health Care: A Leading Cause of Death and Injury. National Academy Press, Washington, DC, 1999, pp. 22-41.

* cited by examiner

APPARATUS, SYSTEM AND METHOD FOR ADMINISTRATION OF A SUBSTANCE

FIELD OF THE INVENTION

The present disclosure relates to an infusion control valve adapted to be actuated by a valve actuator. The present disclosure further relates to an infusion valve actuator adapted to actuate an infusion control valve upon being triggered by an authentication unit. Furthermore, the present disclosure relates to methods for the administration of a substance.

BACKGROUND

The parenteral administration of medications, vitamins, pharmaceuticals, fluids, and the like are among the common medical, therapeutic or similar health or lifestyle interventions with an approximated more than one million infusions daily in the United States. Among the substances that are often administered intravenously, for example, are chemotherapeutic agents, antibiotics, anesthetics, blood and blood components, vitamins, minerals, fluids (such as blood plasma, saline solution, and the like) and total parenteral nutrition (TPN). Chemotherapeutic agents may also be administered by the intrathecal route. When administering a substance by the parenteral route, critical factors affecting safety and efficacy include the proper identification of the substance (such as a drug, a pharmaceutical composition, blood, a blood product, a blood component, plasma, a plasma derivative, a biological substance, total parenteral nutrition or the like), the dose, the rate, timing and route of administration and the like. Errors in these parameters or worse—the administration of parenteral drugs to the wrong patient—will often cause serious side effects, including in some cases, death.

In its landmark 1999 report—*To Err is Human: Building a Safer Health System* by Kohn L T, Corrigan J M, Donaldson M S, eds. National Academy Press, Washington, D.C., incorporated herein by reference, the United States Institute of Medicine indicated that medical errors currently result in more than 50,000 deaths annually, making it the 8$^{th}$ leading of cause of death in the United States, greater than motor vehicle accidents, breast cancer and AIDS. The overall cost of such medical errors was estimated to be between $17-29 billion per year. Sixty-one (61%) of the most serious and life-threatening potential adverse effects were related to the intravenous administration of drugs. Thus, errors in intravenous drug administrations were common, and were reported to occur in nearly 50% of instances of intravenous administrations; approximately 1% of these errors were considered potentially severe (Taxis K, Barber N. Ethnographic study of incidence and severity of intravenous drug errors. Brit J Med 326:684, 2003). Similarly, in pediatric inpatients intravenous (IV) medication errors accounted for up to 54% of adverse drug events (Kaushal R, Bates D W, Landrigan C, et al. Medication errors and adverse drug events in pediatric inpatients. JAMA 285:2114-2120, 2001). The majority of these noted errors occurred at the times of the intravenous administration, and virtually all were reportedly due to human error.

Blood transfusion is a more complex endeavor than the usual intravenous drug infusion because a patient's blood sample must be provided for blood typing before the substance (blood or blood components) is administered. Errors have been found to be frequent in blood transfusion (Sazama K. Reports of 355 transfusion-associated deaths" 1976-1985. Transfusion 30:583-590, 1990, incorporated herein by reference). Thus, in one ongoing surveillance study in the transfusion arena—The Serious Hazards of Transfusion (SHOT) study, Serious Hazards of Transfusion (SHOT), Annual Report, 2003, incorporated herein by reference, which was implemented in the UK between the years 1996-2003, more than 66% of all serious hazards resulted from incorrect blood component administration (1,451 events out of 2,191 serious incidents reported) (Serious Hazards of Transfusion (SHOT), Annual Report, 2003, incorporated herein by reference). In another study Linden J V, Wagner K, Voytovich A E, Sheehan J. Transfusion errors in New York State: an analysis of 10 years' experience. Transfusion 40:1207-1213, 2000, incorporated herein by reference, which reviews transfusion errors in New York State over a 10-year period, it was found that the erroneous administration of blood occurred in 1/14,000 transfusion. With approximately 12 million blood transfusions reportedly administered in the United States annually, this extrapolates to nearly a thousand estimated erroneous transfusions annually in the United States alone. In that study, about 50% of errors occurred outside the blood bank, usually at the patient's bedside, and more than 90% were caused by human mistakes (such as administration of unit(s) of blood to the wrong patient).

SUMMARY

In one embodiment, the invention provides an authentication unit including, inter alia, a patient details acquisition unit, a liquid characteristics acquisition unit, a comparison unit adapted to calculate a correlation value between the details and the characteristics and a valve actuator control unit adapted to trigger an infusion valve actuator if the correlation value is higher than a predetermined threshold value ($V_{th}$).

In another embodiment, the invention provides an infusion control valve adapted to be actuated by a valve actuator, wherein the valve actuator is adapted to be triggered by an authentication unit.

In another embodiment, the invention provides an infusion valve actuator adapted to actuate an infusion control valve upon being triggered by an authentication unit.

In another embodiment, the invention provides a method for delivering an infusion including, inter alia, triggering an infusion valve actuator adapted to actuate an infusion control valve.

DETAILED DESCRIPTION

Figure 1:
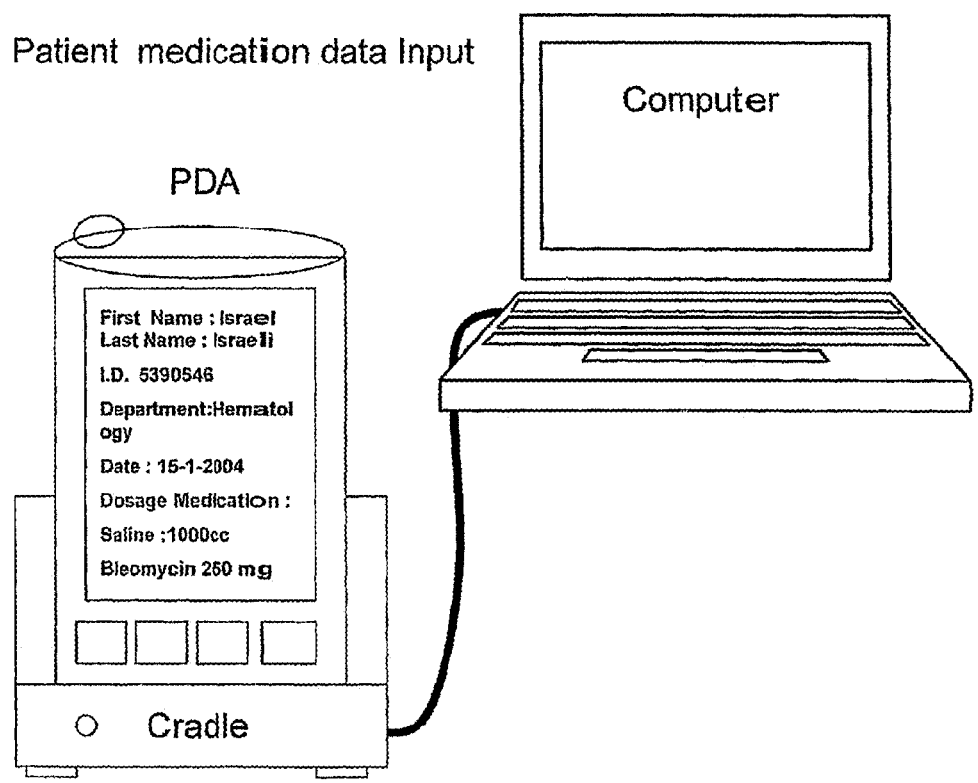
FIG. 1 schematically shows a basic information system, according to embodiments of the invention.

Numerous specific details are set forth herein in order to provide a thorough understanding, however, it will be understood by those of ordinary skill in the art that the present technology may be practiced without the specific details disclosed herein. In other instances, well-known methods, procedures, components, devices, systems and circuits, whether incorporated or related may be merely referenced or otherwise not have been described in detail so as not to obscure the present disclosure.

Errors in parenteral drug administration are common and can lead to morbidity and mortality. These errors place an unnecessary and extraordinary burden on the healthcare system both in human terms and financial costs. The vast majority of errors are simply due to human mistakes which are correctable, or at least ameliorated, by taking certain critical tasks in parenteral drug administration out of error-prone human hands.

Devices, methods and/or systems according to some exemplary embodiments may be implemented to assure safety in the parenteral, intravenous or the like administration of substances such as drugs, pharmaceuticals or the like by inhibiting their administration, for example, until one or more (pre-selected, threshold or dynamic) criteria are met, For example, the parenteral administration of drugs may be inhibited (using for example, mechanical means, a magnetic interlock, an electro-mechanical solenoid or any other appropriate means of inhibition) until one or more of the following events have taken place and/or have been verified:
1. The physician's specific orders for a specific patient have been written and entered into a computer or other control system.
2. The substance the patient is about to receive is identified, for example, electronically, and verified, for example, for accuracy of contents, dosage and/or time of administration, and the like.
3. The patient is identified electronically and is found to be "compatible" with the drug and/or its particulars (for example, dose, sequence with other drugs, rate of administration, time of administration and the like).

In accordance with embodiments of the invention, an activation device may be, for example, is automatically actuated which in turn will open a closed Shutoff Device ("Smart Valve"), permitting the patient to receive the parenteral medicine, for example, once one or more of these parameters have been verified. Conversely, the Shutoff Device may remain in the closed position and the patient may not be able to receive the drug, for example, if the intended recipient of the infusion/transfusion is the wrong patient, and/or the drug is incorrect in kind, dosage or timing. In this manner, the majority and the most severe errors of parenteral drug administration may be prevented.

In addition, systems, methods and/or devices according to some exemplary embodiments of the invention may be implemented to collect and/or store information that may be utilized for the overall, long-term management of the patient's parenteral drug program. This may include, for example, a library of acceptable drug dosages and protocols, precise drug administration history, records of who were the caregivers for each therapeutic event, drug side effects, and/or other critical information and records. This may also help to prevent errors and may assist the medical staff in monitoring the patient's progress and in planning future therapeutic events.

Devices, methods and/or systems according to some exemplary embodiments of the invention may include one or more of the following elements, for example, to assure infusion/transfusion safety:
1. A data authentication unit which may include, inter alia, one or more of the following elements:
    an information containing system;
    a data acquisition unit (which may include, inter alia, a patient details acquisition unit, a liquid characteristics acquisition unit or a combination thereof);
    a comparison unit (which may also be referred to as an identification system); and
    a valve actuator control unit.
2. An infusion valve actuator (may also be referred to as an infusion activation device or a "Smart Activator").
3. An infusion control valve (may also be referred to as an infusion Shutoff Device or a "Smart Valve").

A Data Authentication Unit

In one embodiment, the invention provides an authentication unit including, inter alia, a patient details acquisition unit, a liquid characteristics acquisition unit, a comparison unit adapted to calculate a correlation value between the details and the characteristics and a valve actuator control unit adapted to trigger an infusion valve actuator if the correlation value is higher than a predetermined threshold value.

In another embodiment, the control unit is adapted to remotely trigger the infusion valve actuator.

In another embodiment, the patient details may include, inter alia, patient's identification number, patient's Social Security Number, age, gender, diagnosis, substances to which the patient is allergic, diseases, physical conditions, origin, medical history, physician's orders or any combination thereof. In another embodiment, the patient details may include, inter alia, administration details. In another embodiment, the administration details comprise dosage, timing of administration, rate of administration, sequence of administration with other drugs or any combination thereof.

In another embodiment, the liquid characteristics may include, inter alia, liquid type, content, quantity, intended dosage form, volume, color, density, turbidity, contra indications or any combination thereof.

In another embodiment, the liquid may include, inter alia, saline, a drug, a pharmaceutical composition, blood, a blood product, a blood component, plasma, a plasma derivative, a biological substance, total parenteral nutrition (TPN) or any combination thereof. In another embodiment, the drug may include, inter alia, a chemotherapeutic agent, antibiotics, anesthetics or any combination thereof.

In one embodiment of the invention, the patient details acquisition unit may include, inter alia, means of bar-code, RFID, fingerprints identification, retinal identification, any combination thereof or any other appropriate means of identification.

In another embodiment, the liquid characteristics acquisition unit may include, inter alia, means of bar-code, RFID, any combination thereof or any other appropriate means of identification.

In another embodiment, the authentication unit may be located in a hand held computer, stationary computer or a combination thereof. In another embodiment, any data related to the invention may be stored on a disk on key.

In another embodiment, the comparison unit may include, inter alia, a processing unit.

In another embodiment, the terms remotely trigger, remotely triggering, remotely triggered and the like, may include inter alia, means of IR (Infra Red), RF (Radio Frequency), ultrasound, any combination thereof or any other means of remotely triggering. In another embodiment, the remotely triggering may be done using Bluetooth.

In another embodiment, the valve actuator may be adapted to actuate an infusion control valve upon being triggered by the actuator control unit.

According to some exemplary embodiments of the invention, FIG. 1 describes a portion of the data acquisition and the information containing systems. A physician may enter orders for a specific patient into a computer. The computer may be of a standard format, a hand-held device, or another electronic device of similar capabilities. The computer may have, or may receive, for example, a unique patient identifier such as a bar-code readable number, which may be a Social Security Number, and identification number or any other unique identifier. In addition, other basic patient information such as, but not necessarily limited to, date of birth, gender, diagnosis, and past medication history may be found in the information system.

According to some exemplary embodiments of the invention, for parenteral infusions and/or transfusions the physician may enter the medications to be administered, dosages, date, time, route and duration of administration, and sequence of administration (if necessary). The information system may also contain a library of accepted protocols and dosages to assure that the physician has entered his orders appropriately. The physician's drug orders may be transferred to a hand-held device as illustrated in FIG. 1, in accordance with embodiments of the invention.

Figure 2:
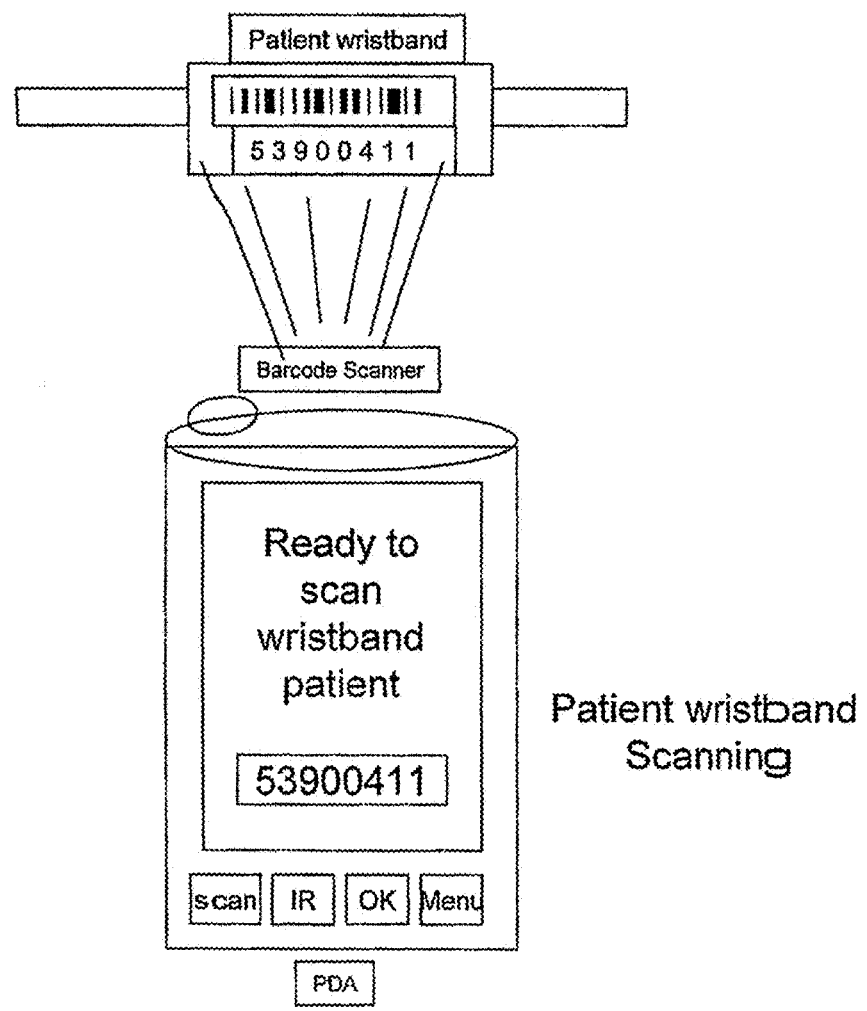
FIG. 2 schematically shows a basic identification system, according to embodiments of the invention.

According to some exemplary embodiments of the invention, FIG. 2 illustrates a portion of the patient's identification system. Patient's identification according to some exemplary embodiments of the invention. In the illustration, the hand-held device may be used to scan the patient's wristband to identify which patient is to be treated, for example, when the infusion or transfusion is ready to be administered. In this illustration, a bar-code identification system is shown, but the invention is not limited to bar-code reading only, and other methods of identification may be used.

The identifier on the patient (for example, bar-code or RFID tag), may be placed on the wrist during hospital admission or at any other time prior to the planned infusion or transfusion. In some environments, the information system may generate the unique identifier that will be placed on the patient. Additionally or alternatively, inherent patient identifiers such as fingerprints, retinal scans or other appropriate identifiers may be used as well.

Figure 3:
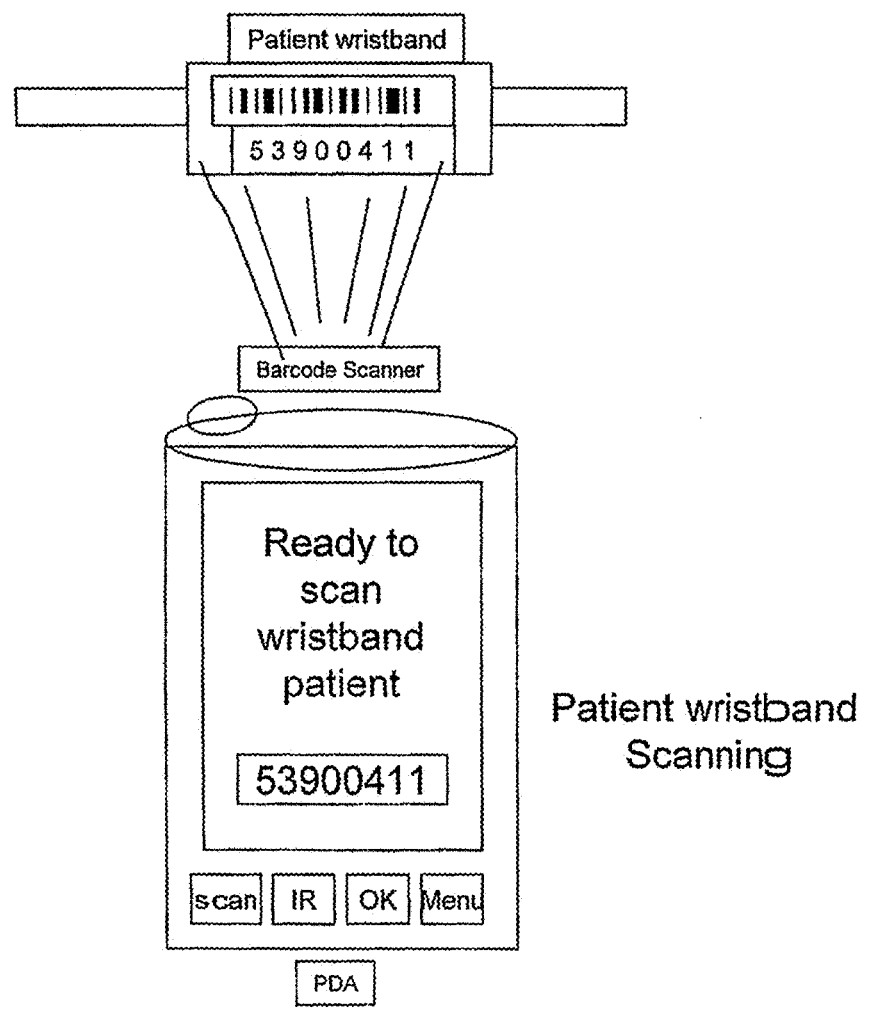
FIG. 3 schematically shows the operation of the activation device ("Smart Card"), the valve (in a closed position) located above the drip chamber and the infusion bag, according to embodiments of the invention.

Once the patient is identified, the drug to be administered is similarly identified by scanning the infusion bag. This is illustrated in FIG. 3, according to some exemplary embodiments of the invention. The scanning may identify the medication and the dose present in the bag and will likely be appended by the person preparing the infusion. In FIG. 3 a bar-code identification system is shown, but other information methods can also be employed. This identification may be implemented to correlate the drug to be administered with the patient. The information may transmitted back to the hand-held device to assure that the specific patient is due to get the specific medication, at this dose and at this time, for example, after both the patient and the medication are scanned. This may be performed, for example, by checking, for example, electronically, the information in the computer with the scanning information.

An Infusion Valve Actuator (Infusion Activation Device or "Smart Activator")

In one embodiment, the invention provides an infusion valve actuator adapted to actuate an infusion control valve upon being triggered by an authentication unit.

In another embodiment, the actuator is adapted to actuate the valve upon being remotely triggered by the authentication unit.

In another embodiment, the infusion valve actuator may be adapted to actuate the infusion control valve by mechanical, electrical, electromechanical, magnetic means or any combination thereof. In another embodiment, the infusion valve actuator may be adapted to remotely actuate the infusion control valve.

In another embodiment, the infusion valve may be adapted to allow the flow of the infusion liquid upon being actuated. In another embodiment, the infusion valve may be adapted to inhibit the flow of the infusion liquid when the valve is not actuated.

In another embodiment, the infusion control valve may include, inter alia, a key cylinder.

In another embodiment, the key cylinder is adapted to allow the flow of the infusion liquid upon being actuated by the rotation of a key within the key cylinder.

In another embodiment, the infusion valve actuator may be adapted to remain attached to the valve after actuation. In another embodiment, the infusion valve actuator may be adapted to disconnect from the valve after actuation.

In another embodiment, the authentication unit may include, inter alia, a patient details acquisition unit, a liquid characteristics acquisition unit, a comparison unit adapted to calculate a correlation value between the details and the characteristics and a valve actuator control unit adapted to trigger an infusion valve actuator if the correlation value is higher than a predetermined threshold value.

Figure 4:
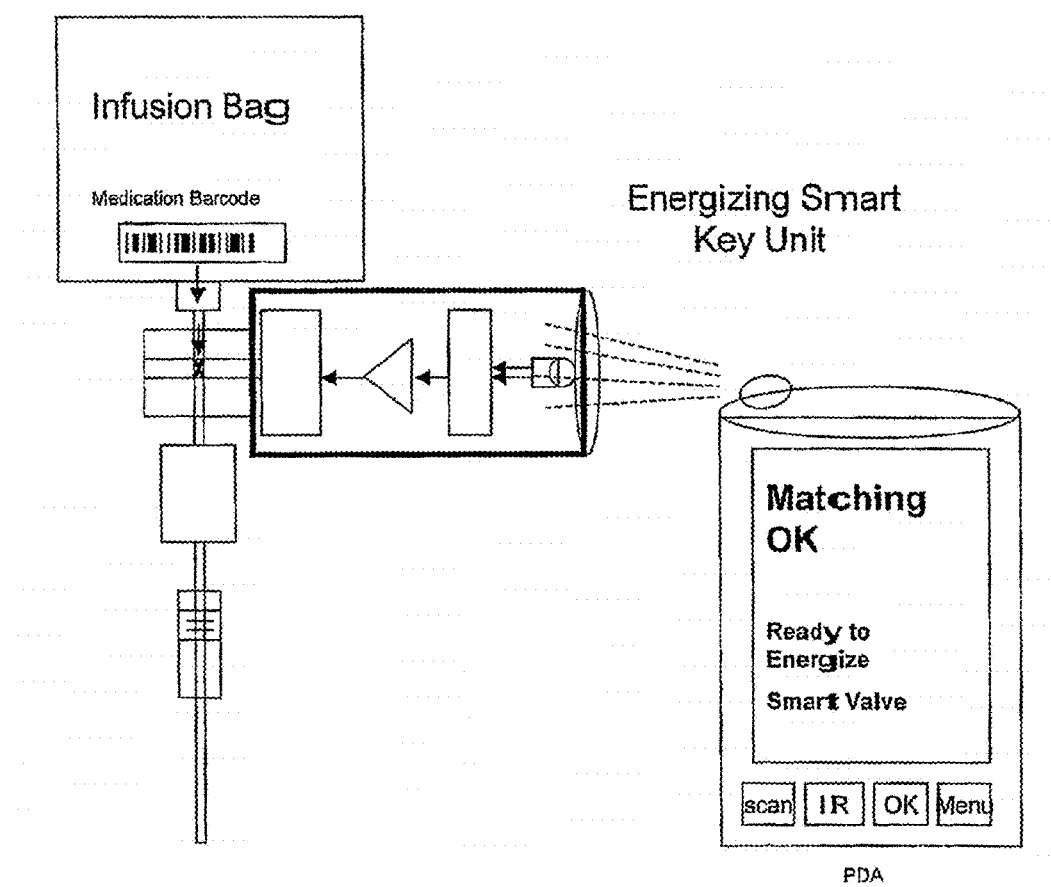
FIG. 4 schematically shows the triggering of the activation device, by a hand-held computer, while the activation device is connected to the valve, according to embodiments of the invention.
Figure 5:
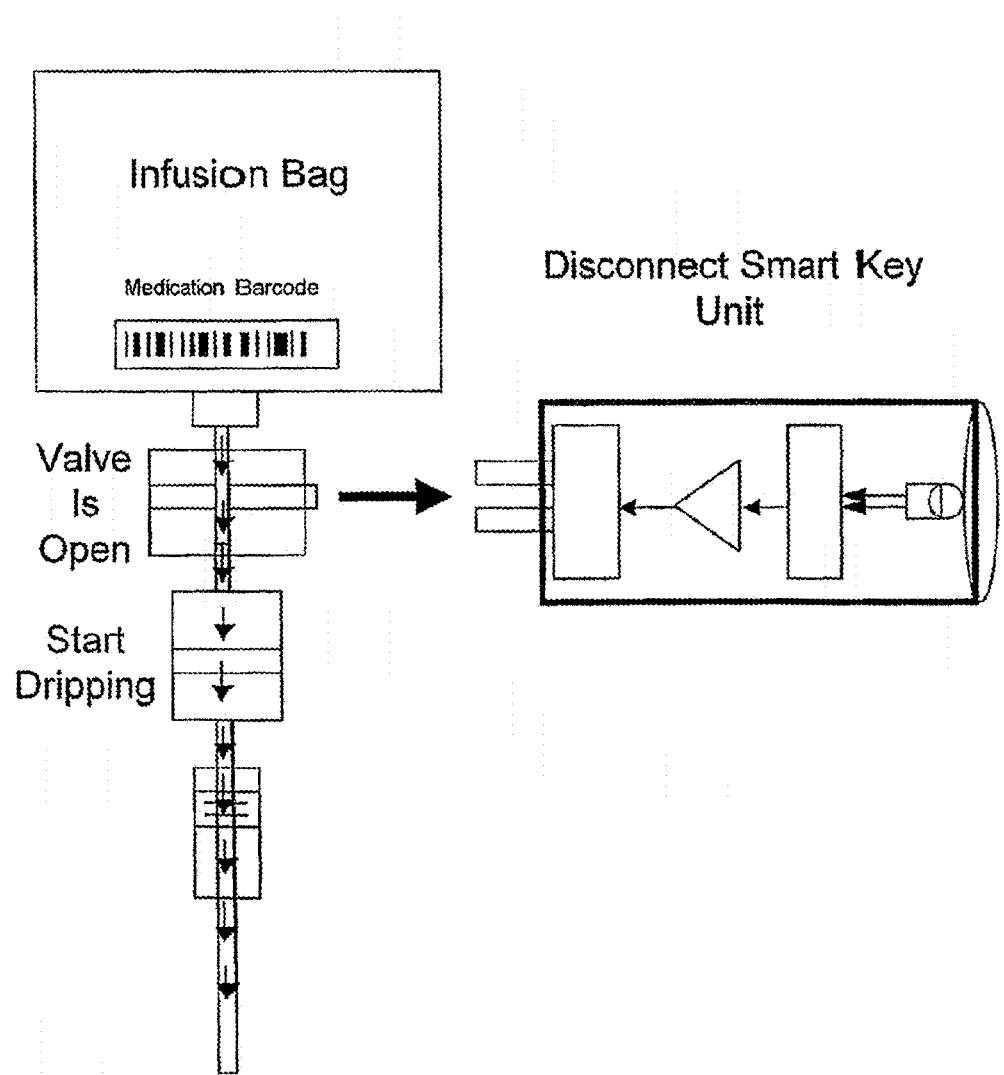
FIG. 5 schematically shows the disconnection of the activation device after the actuation of the valve which now allows the infusion to flow, according to embodiments of the invention.

FIGS. 4 and 5 illustrate the infusion valve actuator (infusion activation device) and its function according to some exemplary embodiments of the invention. the information system may transmit, for example, electronically, instructions to the activation device, for example, after checking the patient's identification and the physician's orders. The device may be instructed, for example, electronically, for example, based on one or more of the previous actions, to be programmed to open or not to open the Shutoff Device, as described below.

According to some exemplary embodiments of the invention, the activation device may be reusable, may receive information regarding whether the infusion or transfusion should proceed, and/or "order" the Shutoff Device to open when drug administration is considered safe. FIG. 4 illustrates that the activation device is actuated, meaning it has received information to open the Shutoff Device. This device may now instruct the Shutoff Device to open and permit the infusion to commence. Once the infusion begins, the activation device can be removed for further use on this or other patients.

In the illustrations, the activation device is shown as a separate "smart card", but other devices may be used as well. The activation device may even be an integral part of the information system, such as part of the hand-held computer and not a separate device.

According to some exemplary embodiments, the activation device may have an "override" feature, which can be used, for example, in emergency situations when infusion without data entry or verification (for example, acute, massive hemorrhage) is necessary.

An Infusion Control Valve (Shutoff Device, "Smart Valve)

In another embodiment, the invention provides an infusion control valve adapted to be actuated by a valve actuator, wherein the valve actuator is adapted to be triggered by an authentication unit. In another embodiment, the invention provides an infusion control valve adapted to be actuated by a valve actuator, wherein the valve actuator is adapted to be remotely triggered by an authentication unit.

In another embodiment, the valve is adapted to allow the flow of the infusion liquid upon being actuated. In another embodiment, the valve is adapted to inhibit the flow of the infusion liquid when the valve is not actuated.

In another embodiment, the valve may include, inter alia, a key cylinder. In another embodiment, the key cylinder is adapted to allow the flow of the infusion liquid upon being actuated by the rotation of a key within the key cylinder.

In another embodiment, the infusion valve is adapted to be actuated by the valve actuator by mechanical, electrical, electromechanical, magnetic means or any combination thereof. In another embodiment, the infusion valve may be adapted to be remotely actuated by the infusion valve actuator.

In another embodiment, the valve may be disposable. In another embodiment, the valve may be made only from polymeric materials. In another embodiment, the valve may be made only from plastic materials. In another embodiment, the valve may be reusable. In another embodiment, the valve may be located outside the liquid path. In another embodiment, the valve may be located within the liquid path. In another embodiment, the valve may be located above the drip chamber. In another embodiment, the valve may be located below the drip chamber. In another embodiment, the valve may be conjugated to the drip chamber. In another embodiment, the valve may be mounted upon the drip chamber. In another embodiment, the valve may be located between an infusion bag and a pump. In another embodiment, the drip chamber may be referred to herein as a "spike".

In another embodiment, the valve may be designed to inhibit the flow of infusion liquid during replacement of an infusion container. In another embodiment, the valve may be designed to inhibit the flow of infusion liquid during replacement of an infusion container by sealing the valve seal upon application of external pressure onto the valve during the replacement of the infusion container. In another embodiment, the valve or the activation device may further include, inter alia, a counter adapted to count the number of infusion drops in the drip chamber.

The Shutoff Device (valve) and the activation device (valve actuator), according to some exemplary embodiments of the invention, may be illustrated in FIGS. 3, 4 and 5. In FIGS. 3 and 4, the valve is shown in the "Closed" position, and the solutions in the infusion bag cannot be administered to the patient. FIG. 3 shows the activation device being put in proximity to the Shutoff Device. FIG. 4 shows that the activation device is actuated, that is, given the signal that the infusion/transfusion may proceed. FIG. 5, shows the Shutoff Device in the open position and the drug is being administered to the patient. Once a single infusion is completed, it can be reused a number of times when changing infusions bags for the same therapeutic event. After each bag change, the Shutoff Device may have to be reopened by repeating the steps leading to activation of the activation device.

Figure 7:
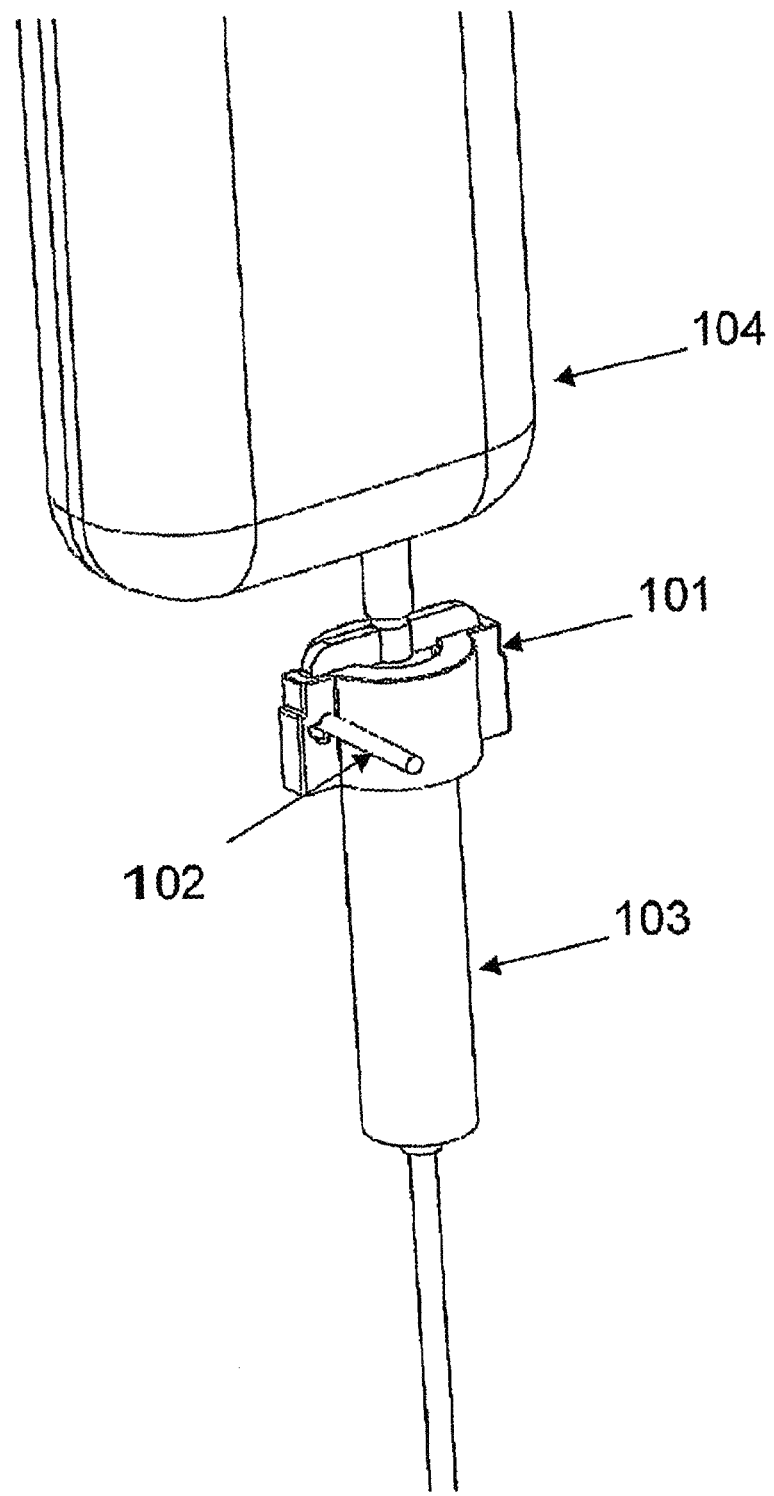
FIG. 7 illustrates a shutoff device, according to embodiments of the invention.

The Shutoff Device may be outside the infusion fluid path or within. According to some embodiments, the Shutoff Device may be positioned above the drip chamber of the infusion set, as illustrated in FIG. 3, 4, 5. The Shutoff Device may also be positioned between the drip chamber and the spike, and conjugated to them, as illustrated in FIG. 7.

Figure 6A:
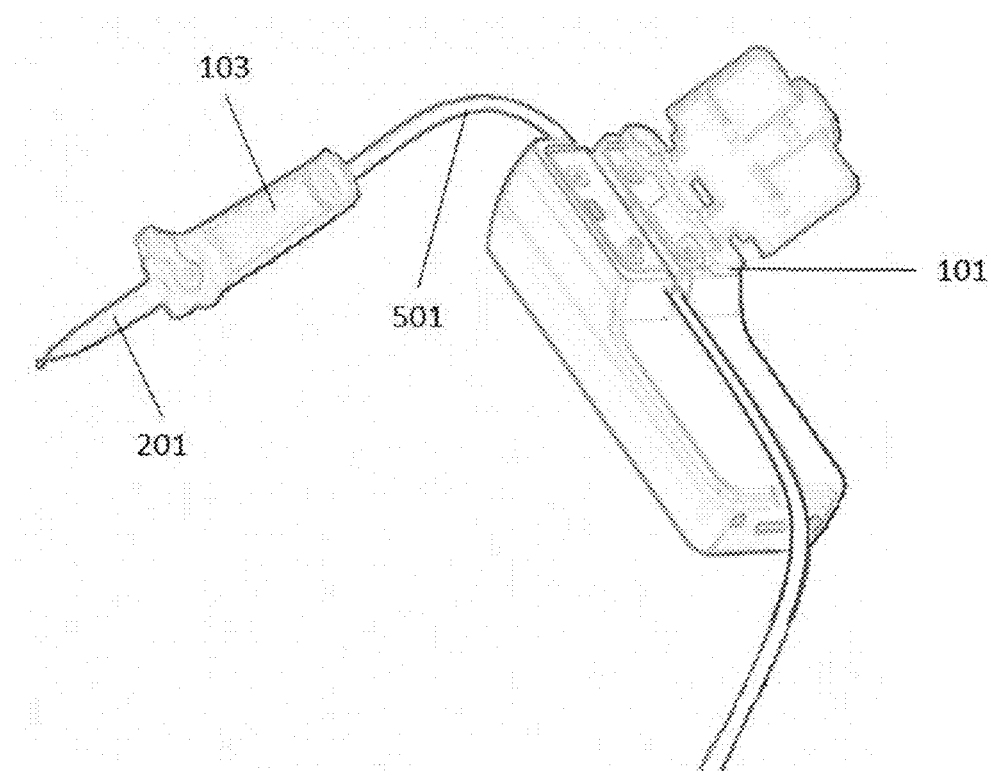
FIG. 6*a* illustrates a shutoff device, positioned below the drip chamber, according to embodiments of the invention.

According to other embodiments, the Shutoff Device may be positioned below the drip chamber. FIG. 6a illustrates, according to some exemplary embodiments, Shutoff Device (101), positioned on infusion line (501), which is in fluid flow connection with drip chamber (103) and spike (201). According to this embodiment, Shutoff Device (101) is not conjugated to spike (201) and/or to drip chamber (103). According to an exemplary embodiment, Shutoff Device (101) may be positioned below drip chamber (103) and spike (201).

Figure 6B:
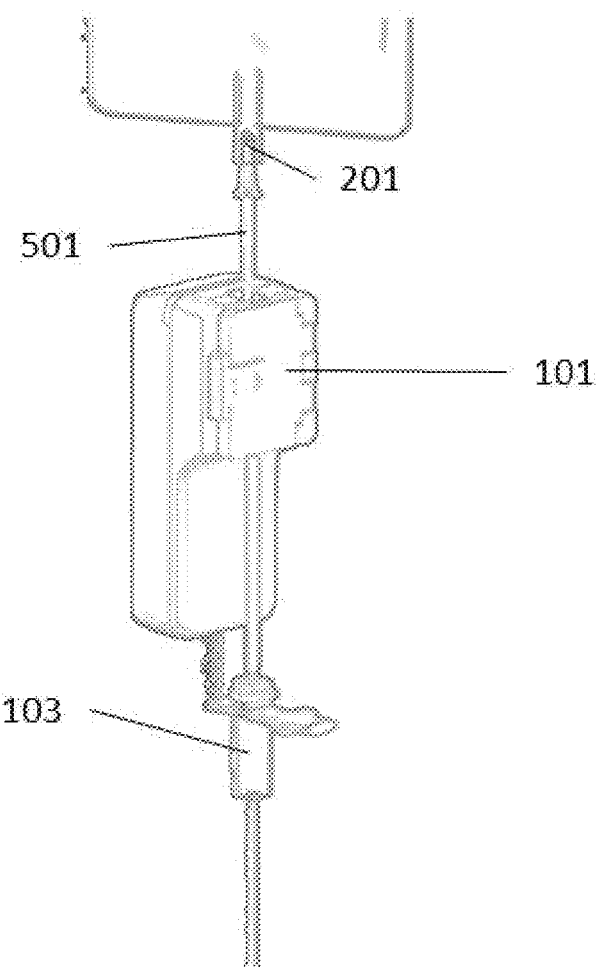
FIG. 6*b* illustrates a shutoff device, positioned above the drip chamber, according to embodiments of the invention.

According to further embodiments, the Shutoff Device may be positioned above the drip chamber of the infusion set and not conjugated to the drip chamber and/or the spike. FIG. 6b illustrates, according to some exemplary embodiments, Shutoff Device (101) positioned on infusion line (501), which is in fluid flow connection with drip chamber (103) and spike (201). According to this embodiment, Shutoff Device (101) is positioned between drip chamber (103) and spike (201) but not conjugated to any of them. According to additional embodiments, other placements on, or in, the infusion line, or on the infusion bag, or a combination of placements, are possible.

In the Figures herein, three possible non-limiting examples of Shutoff Devices are illustrated in detail. The invention may use one or all of these devices, or other devices that perform one or more of the functions described above.

Option 1, according to embodiments of the invention, provides a Shutoff Device which is integrated into the infusion kit, specifically to the drip chamber. In one embodiment of the invention, axial movement of the Shutoff Device components may open and close the liquid path. In another embodiment, upon insertion of the infusion kit drip chamber to the infusion bag, the components may move axially and the Shutoff Device may be automatically closed. In another embodiment, a "key" may be used to open the Shutoff Device. In another embodiment, the key may be a part of the activation device. In another embodiment, the key may be used as a manual override key in, for example, emergency situations. In another embodiment, rotation movement of the key in the Shutoff Device will result in the opening thereof. Option 1 of the Shutoff Device, according to some exemplary embodiments of the invention, may be illustrated in FIGS. 7-14.

FIG. 7 illustrates, according to some exemplary embodiments, a shutoff device (101) which may be actuated or manually opened or closed by a key (102). The Shutoff Device (101) is designed as an integral part of the drip chamber (103).

Figure 8:
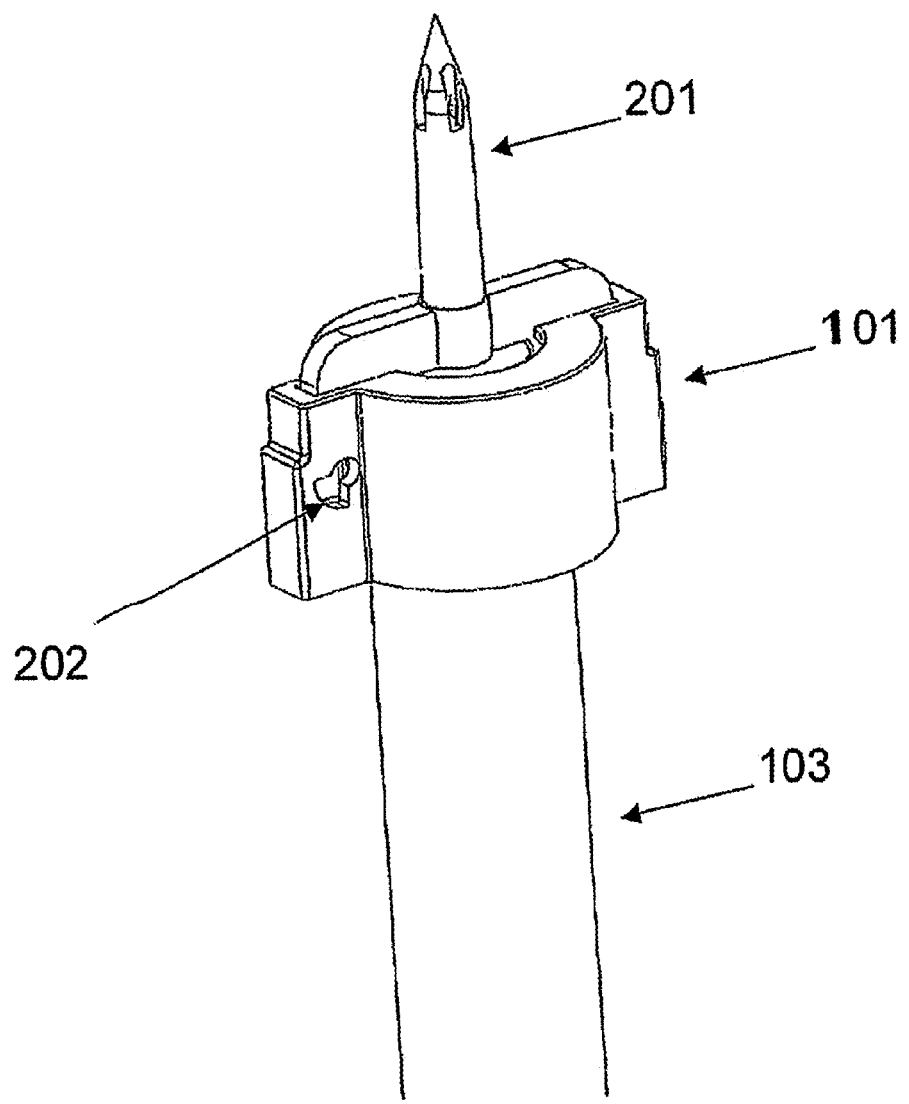
FIG. 8 illustrates a shutoff device, according to embodiments of the invention.

FIG. 8 illustrates, according to some exemplary embodiments, a shutoff device (101) having a spike (201) designed to penetrate into an infusion bag and having a key hole (202) adapted to be actuated or manually opened or closed by a key. The Shutoff Device (101) is designed as an integral part of the drip chamber (103).

Figure 9:
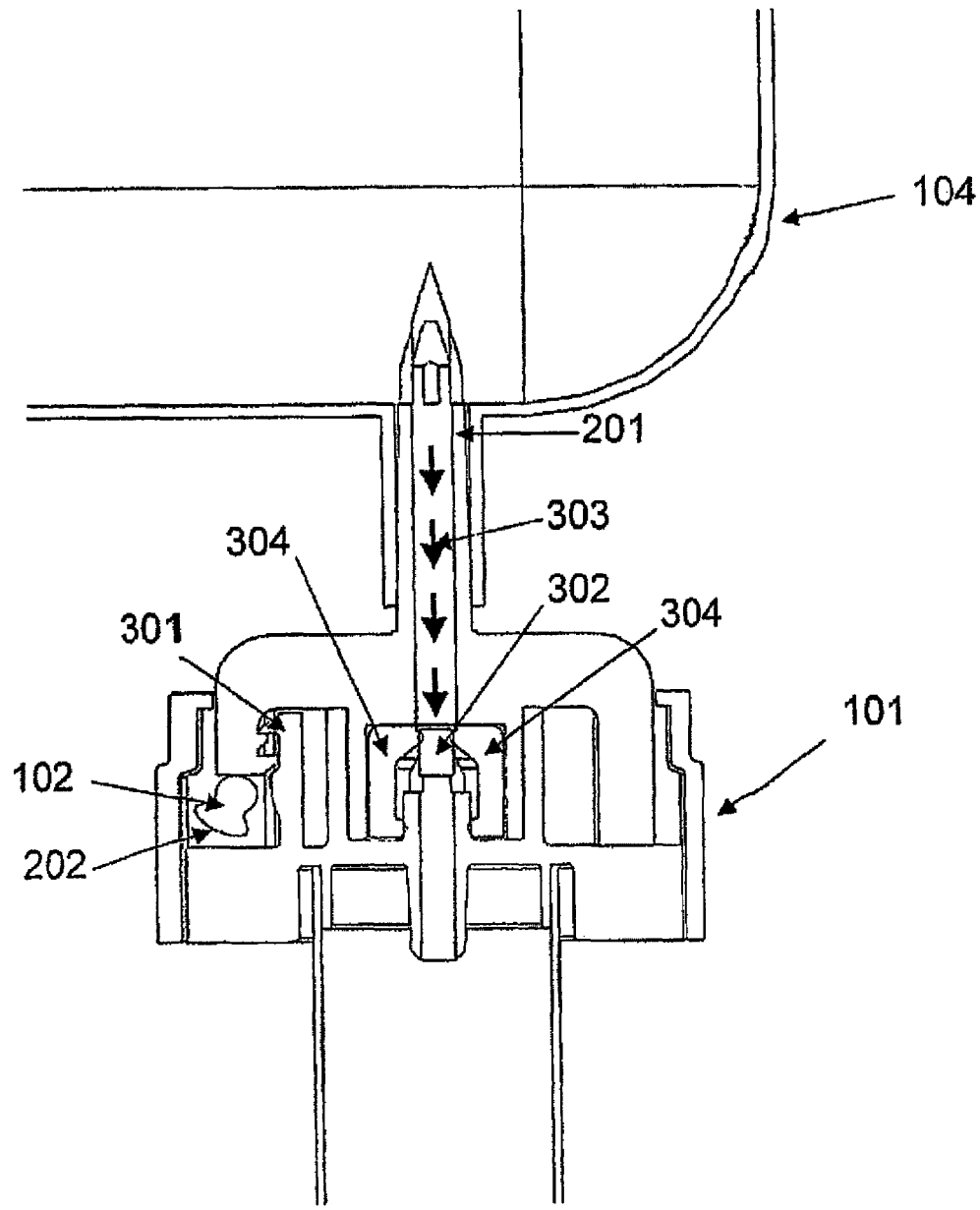
FIG. 9 illustrates a cross section of a shutoff device, according to embodiments of the invention.

FIG. 9 illustrates, according to some exemplary embodiments, a cross section of the shutoff device (101) having a spike (201) designed to penetrate into an infusion bag (104), through which the infusion liquid (303) may pass. The shutoff device (101) includes a locking element (301) which is adapted to change the position of a blocking element (302) which is presented in a closed position, is adapted to allow or inhibit the flow of the infusion liquid (303) when it is in an opened and closed position, respectively. The valve seal (304) is adapted to prevent liquid leaks. A key (102) is inserted in the key hole (202) and has not yet rotated in the key hole.

Figure 10:
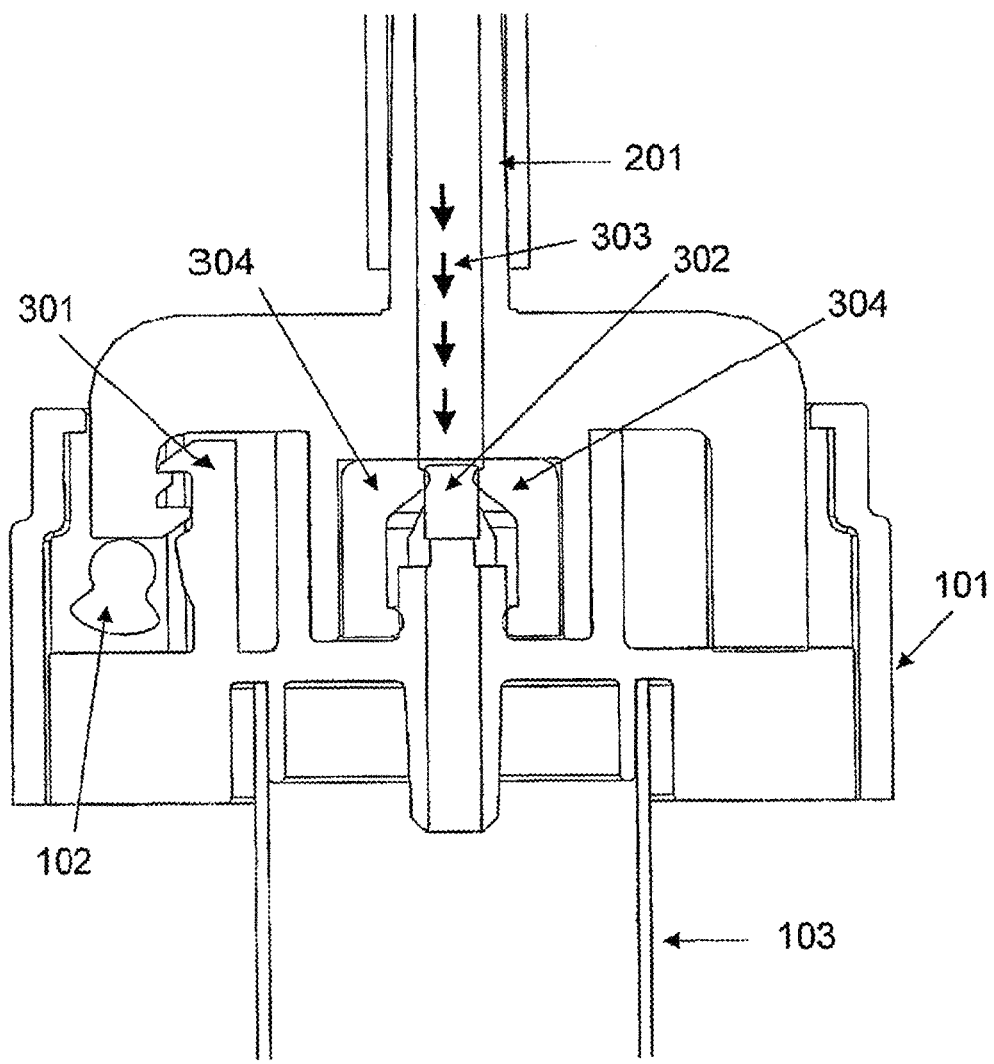
FIG. 10 illustrates a cross section of a shutoff device, according to embodiments of the invention.

FIG. 10 illustrates, according to some exemplary embodiments, a cross section of the shutoff device (101) having a spike (201) designed to penetrate into an infusion bag, through which the infusion liquid (303) may pass. The key (102) is now starting to rotate (relative to its position illustrated in FIG. 10) but the locking element (301) has not changed its position and blocking element (302) is still closed.

Figure 11:
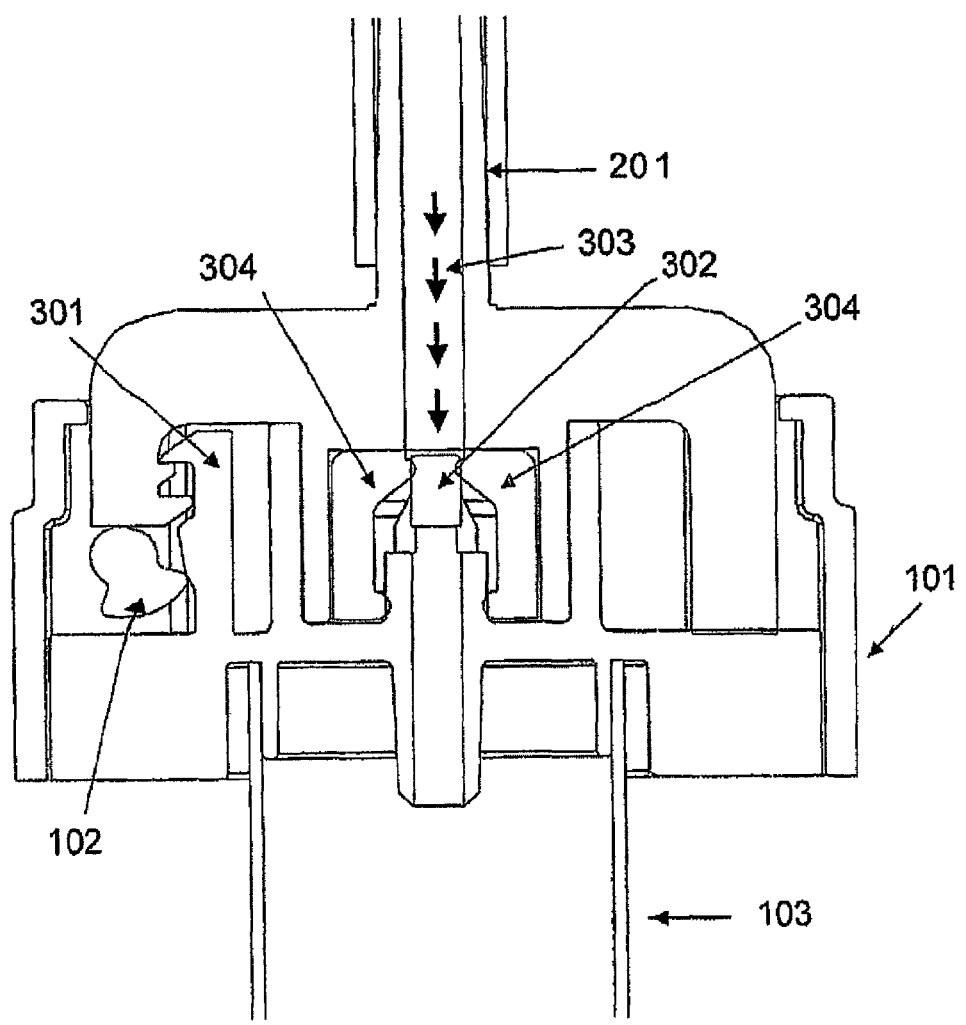
FIG. 11 illustrates a cross section of a shutoff device, according to embodiments of the invention.

FIG. 11 illustrates, according to some exemplary embodiments, a cross section of the shutoff device (101) having a spike (201) designed to penetrate into an infusion bag, through which the infusion liquid (303) may pass. The key (102) continues to rotate (relative to its position illustrated in FIG. 10) and applies pressure on the locking element (301) and pushes it. The blocking element (302) is still closed.

Figure 12:
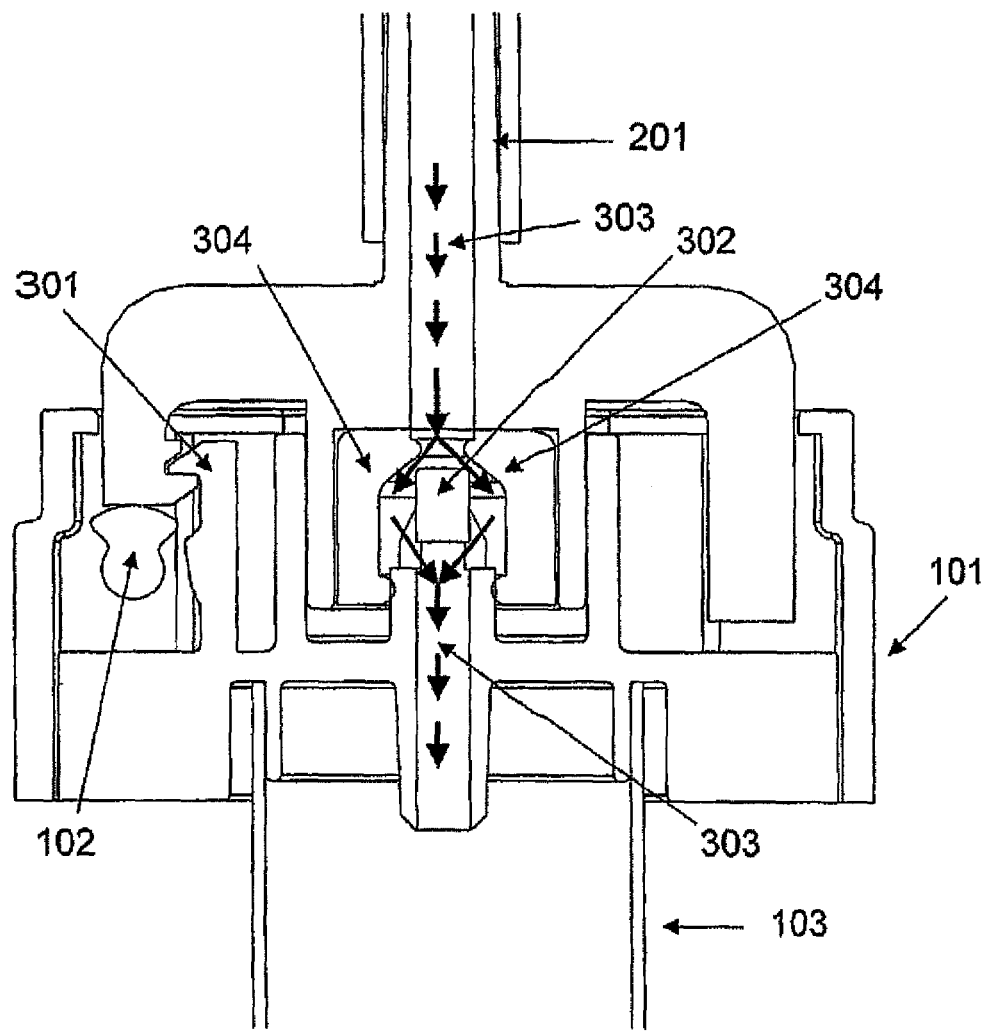
FIG. 12 illustrates a cross section of a shutoff device, according to embodiments of the invention.

FIG. 12 illustrates, according to some exemplary embodiments, a cross section of the shutoff device (101) having a spike (201) designed to penetrate into an infusion bag, through which the infusion liquid (303) may pass. The key (102) continues to rotate (relative to its position illustrated in FIG. 11) and causes the locking element (301) to change its position by bending it away and thus opening the blocking element (302) and allowing the infusion liquid (303) to flow towards the drip chamber (103).

Figure 13:
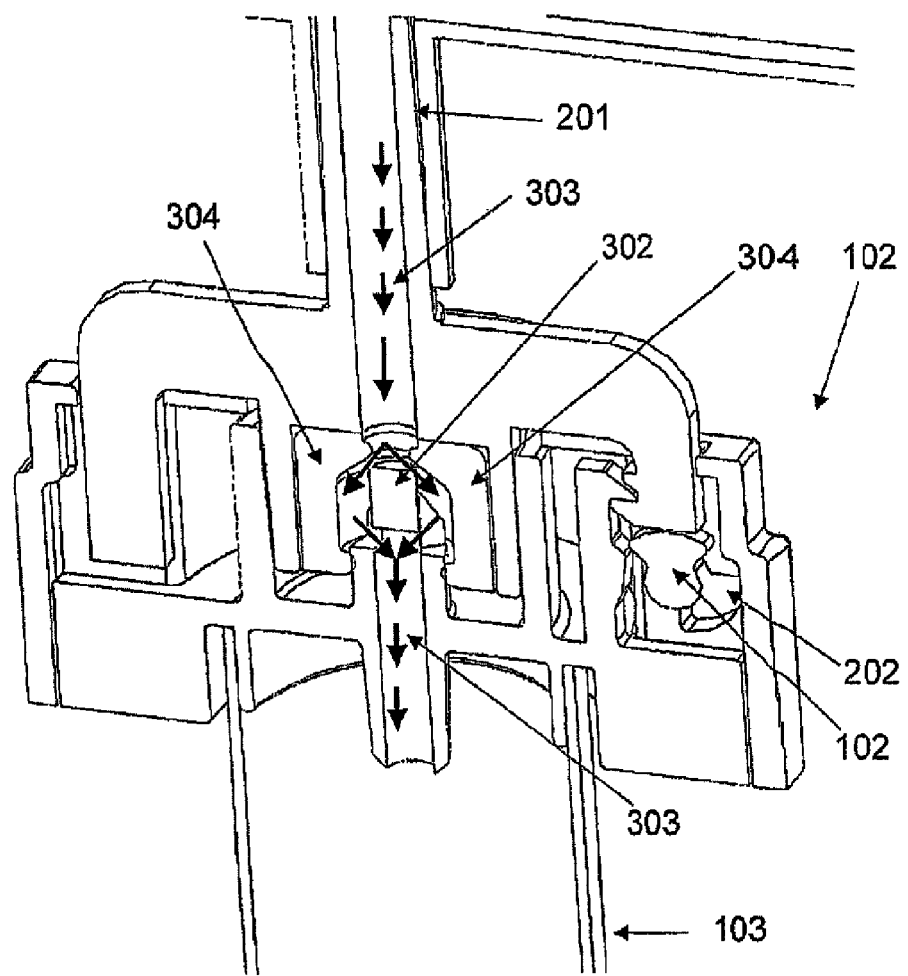
FIG. 13 illustrates a cross section of a shutoff device, according to embodiments of the invention.

FIG. 13 illustrates, according to some exemplary embodiments, in addition to the elements described in FIG. 12, the position of the key (102) relative to the key hole (202). The Key (102) may be removed and the shutoff device may be remained in a opened position.

Figure 14:
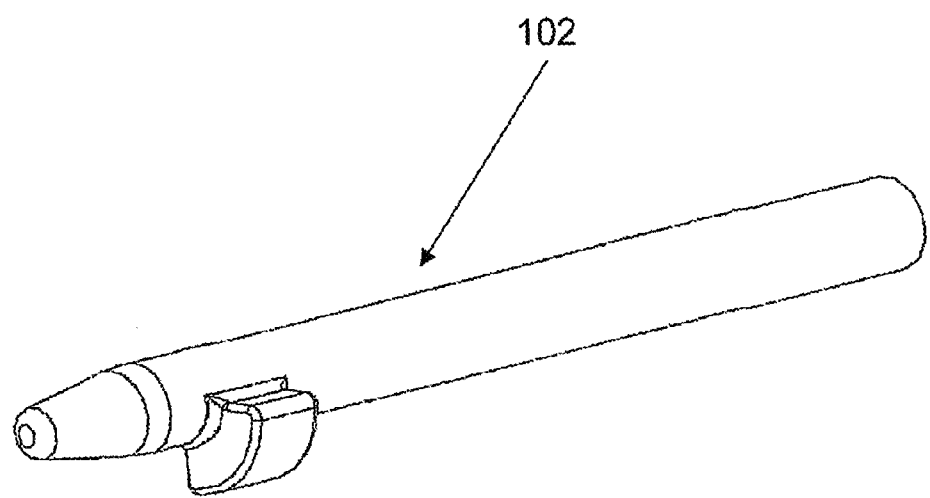
FIG. 14 shows a key according to embodiments of the invention.

FIG. 14 illustrates a key (102), according to some exemplary embodiments.

Option 2, according to embodiments of the invention, provides a Shutoff Device which is an "inline" valve. According to another embodiment, the Shutoff Device may be used with regular infusion kits. According to another embodiment, one end of the Shutoff Device may be connected to the infusion bag and the other end may be connected to the infusion kit. The working principal of the valve, according to some embodiments of the invention may be similar to the working principal of option 1. Option 2 of the Shutoff Device, according to some exemplary embodiments of the invention, may be illustrated in FIGS. 15-17.

Figure 15:
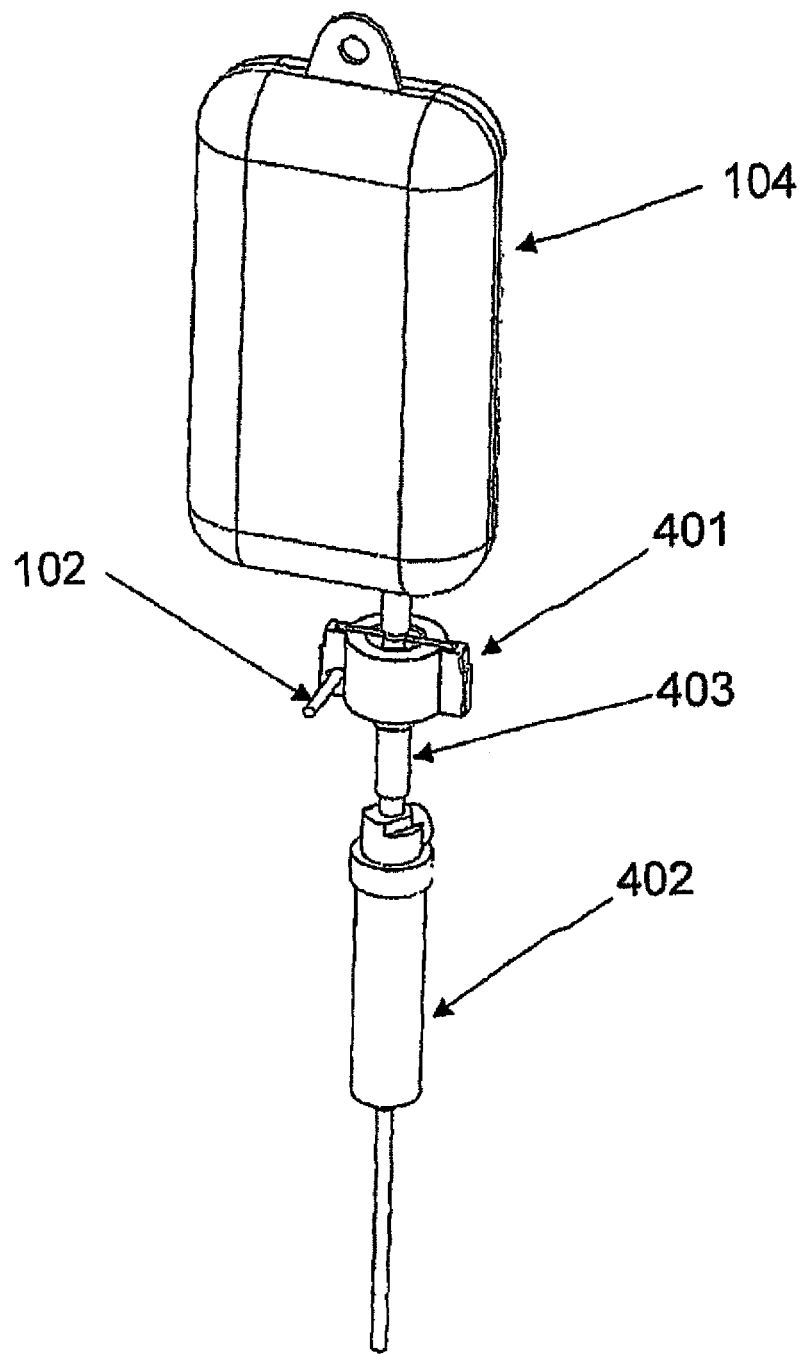
FIG. 15 illustrates a shutoff device, according to embodiments of the invention.

FIG. 15 illustrates, according to some exemplary embodiments, a shutoff device (401) which may be connected on one end to an infusion bag (104) and on the other end to a drip chamber (402) by a connecting element (403) which may be integral with the shutoff device (401). The shutoff device may be actuated or manually opened or closed by a key (102).

Figure 16:
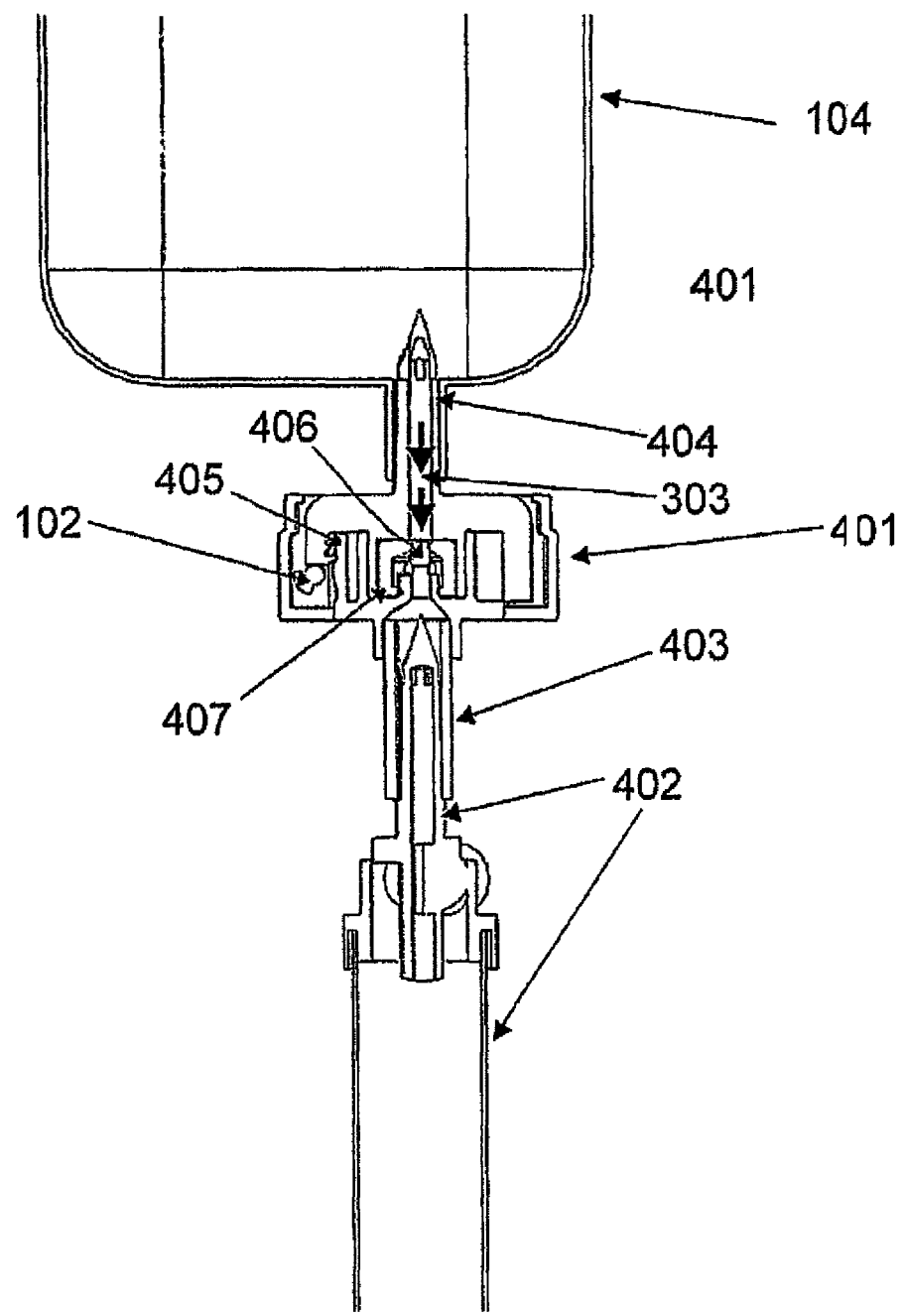
FIG. 16 illustrates a cross section of a shutoff device, according to embodiments of the invention.

FIG. 16 illustrates, according to some exemplary embodiments, a cross section of the shutoff device (401) having on one end a spike (404) designed to penetrate into an infusion bag (104), through which the infusion liquid (303) may pass and on the other end a connecting element (403) designed to connect to a drip chamber (402). The shutoff device (401) includes a locking element (405) which is adapted to change the position of a blocking element (406) which is presented in a closed position, is adapted to allow or inhibit the flow of the infusion liquid (303) when it is in an opened and closed position, respectively. The valve seal (407) is adapted to prevent liquid leaks. A key (102) may be inserted and operate in a similar way as described in option 1.

Option 3, according to embodiments of the invention, provides a Shutoff Device which is adapted to block the fluid flow by "pinching" the infusion line. According to one embodiment of the invention, Shutoff Device may be an add-on system on the infusion kit. In another embodiment, the axial movement of the drip chamber relative to the valve's external parts may close the fluid flow. In another embodiment, upon insertion of the spike into the infusion bag the valve's components may move axially and the valve may close automatically. In another embodiment, a key may be used to open the valve. Option 3 of the Shutoff Device, according to some exemplary embodiments of the invention, may be illustrated in FIGS. 18-19.

Figure 17:
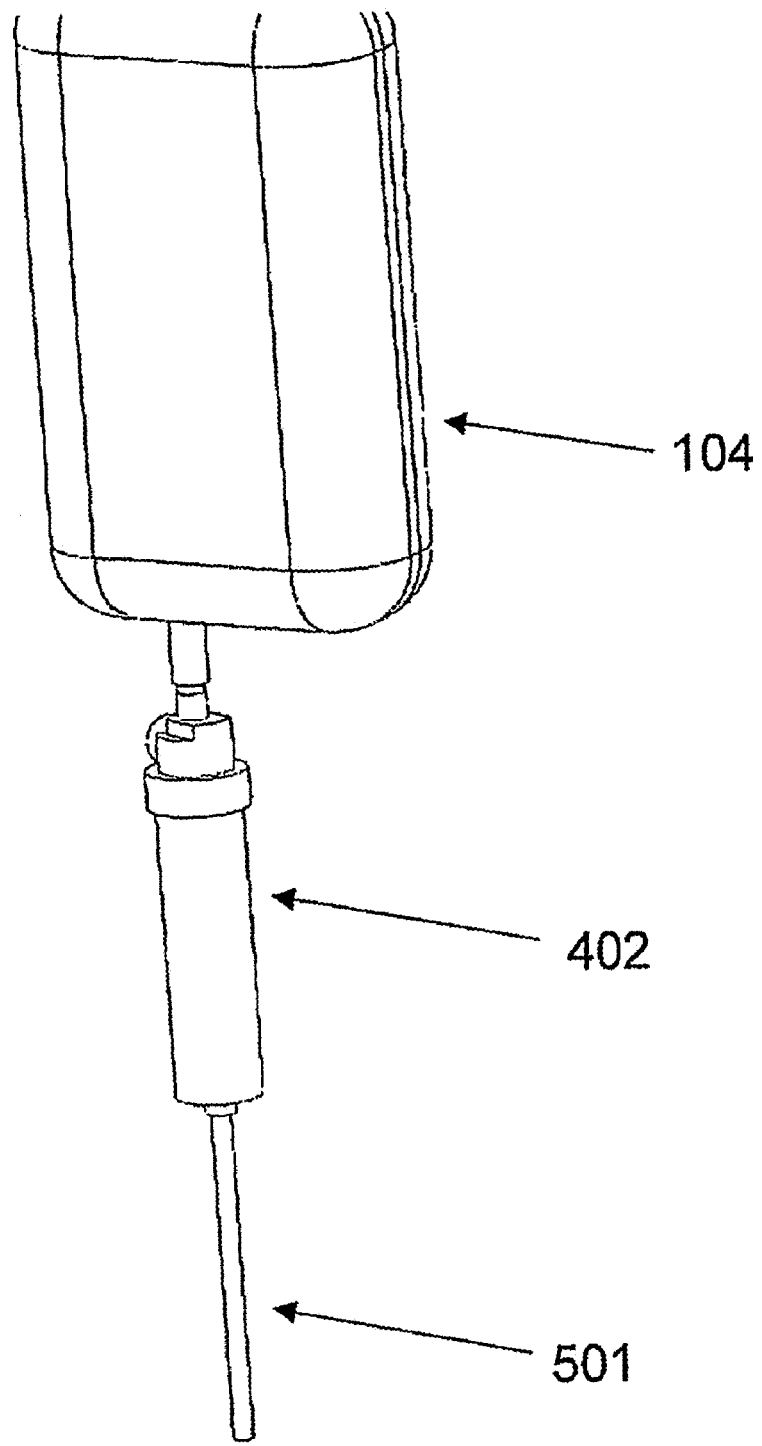
FIG. 17 shows a typical infusion kit.

FIG. 17 illustrates, according to some exemplary embodiments, a regular infusion kit having an infusion bag (104), a drip chamber (402) and the infusion line (501).

Figure 18:
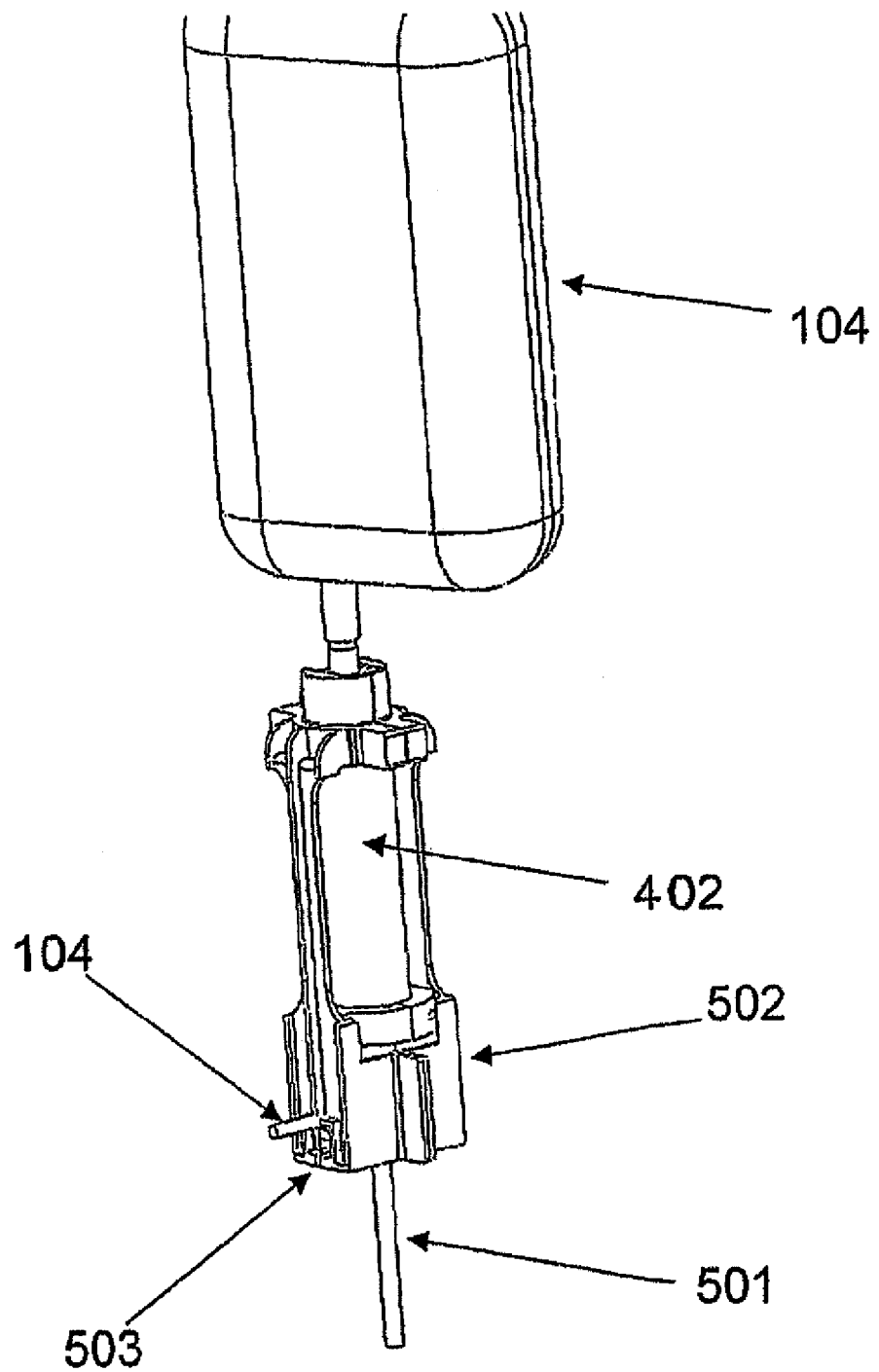
FIG. 18 shows an add-on shutoff device according to embodiments of the invention.

FIG. 18 illustrates, according to some exemplary embodiments, a shutoff device (502) placed on the drip chamber (402), having a pinching mechanism (503) which may be operated by a key (102). The pinching mechanism may pinch the infusion line (501) and block the liquid flow.

In another embodiment, the invention provides a method for delivering an infusion including, inter alia, triggering an infusion valve actuator adapted to actuate an infusion control valve. In another embodiment, the invention provides a method for delivering an infusion including, inter alia, remotely triggering an infusion valve actuator adapted to actuate an infusion control valve.

In another embodiment, the delivering may include, inter alia, intravenous administration. In another embodiment, the delivering may include, inter alia, parenteral administration. In another embodiment, the delivering may include, inter alia, epidural administration. In another embodiment, the delivering may include, inter alia, intrathecal administration. In another embodiment, the delivering may include, any form of administration of any substance which substance needs to be identified prior to administration.

In another embodiment, the method may further include, inter alia, removing the actuator from the valve after actuation.

Figure 19:
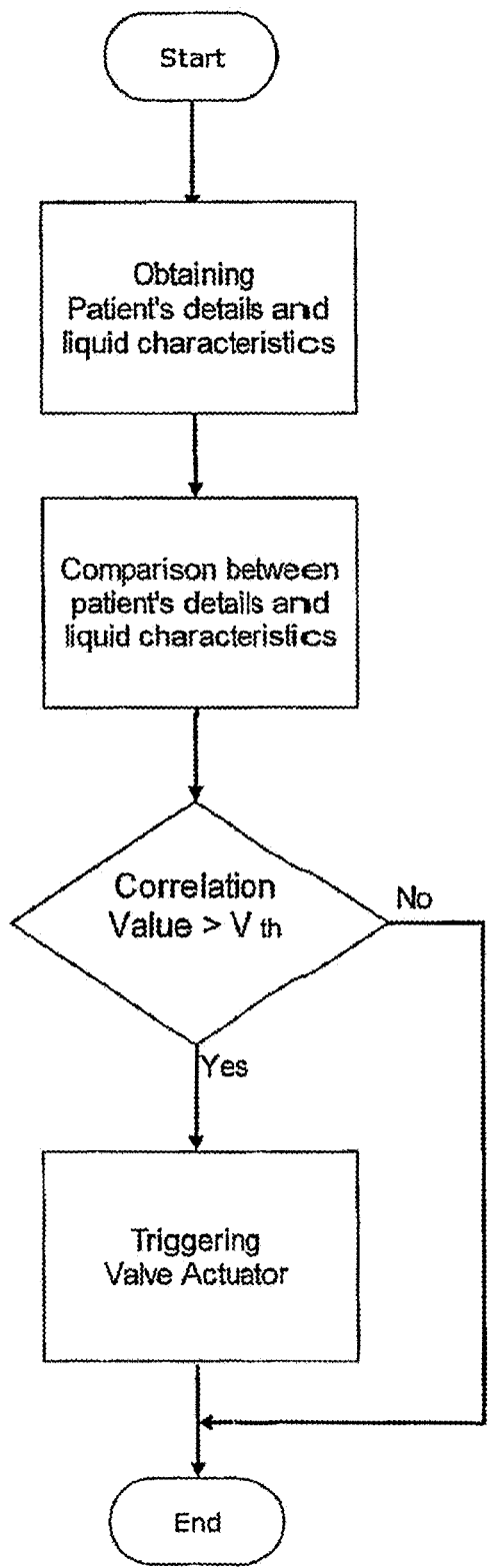
FIG. 19 shows a flowchart of a method according to embodiments of the invention.
Figure 20:
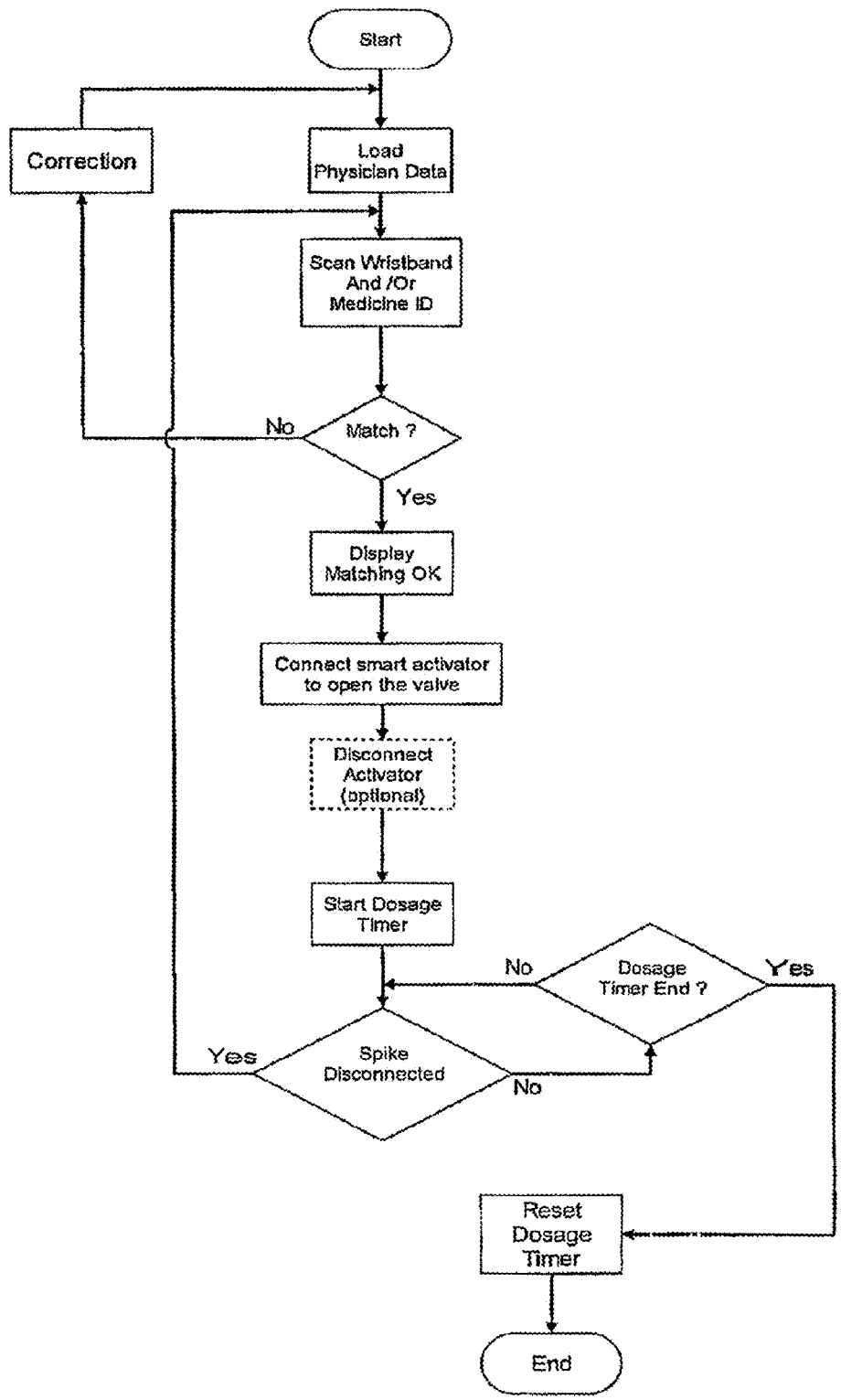
FIG. 20 shows a flowchart of a method according to embodiments of the invention.

FIGS. 19 and 20 describe flowcharts a according to some exemplary embodiments of the invention.

FIG. 19 illustrates a flow chart of a method, according to some exemplary embodiments. Data relating to the patient and to the administered liquid may be obtained and a correlation analysis between the data sets may be conducted yielding a correlation value. If the correlation value is higher than a predetermined threshold value ($V_{th}$) the valve actuator is triggered. The valve actuator may open a valve, which was initially in a closed position. If the correlation value is lower than a predetermined threshold value ($V_{th}$) the valve actuator is not triggered.

FIG. 20 illustrates a flow chart of a method, according to some exemplary embodiments. Data obtained from a physician is loaded and optionally transferred to a hand held computer. Data relating to the patient and to the administered liquid may be scanned and a correlation analysis between the data sets may be conducted yielding a match. If there is no match, a correction is performed (for example, changing the infusion to the right infusion or going to another patient). If there is a match, the result is displayed and the smart activator (valve actuator) is connected to the valve and opens it. The dosage timer may be started. If the timer ends it may be reset. If the infusion bag is removed or replaced (by disconnecting the spike) the valve may be automatically closed and the medicine has to be rescanned. The smart activator may or may not be disconnected from the valve. the valve actuator is triggered. The valve actuator may open a valve, which was initially in a closed position. If the correlation value is lower than a predetermined threshold value ($V_{th}$) the valve actuator is not triggered.

In one embodiment of the invention, the term "infusion" may be defined as any substance adapted for administration to a subject. In another embodiment the substance may be a liquid. In another embodiment the substance may include particles. In another embodiment the substance may include a gel. In another embodiment, the infusion may be adapted for intravenous administration. In another embodiment, the infusion may be adapted for parenteral administration. In another embodiment, the infusion may be adapted for epidural administration. In another embodiment, the infusion may be adapted for intrathecal administration. In another embodiment, the infusion may be adapted for any form of administration of any substance which substance needs to be identified prior to administration. In another embodiment, the term infusion may include transfusion.

In another embodiment, the term infusion as referred to herein may include, inter alia, saline, a drug, a pharmaceutical composition, blood, a blood product, a blood component, plasma, a plasma derivative, a biological substance, total parenteral nutrition (TPN), any combination thereof or any other substance that is adapted to be may be administered to a subject. In another embodiment, the drug may include, inter alia, a chemotherapeutic agent, antibiotics, anesthetics, any combination thereof or any other substance that is adapted to be may be administered to a subject.

In one embodiment of the invention, the term "infusion" may refer to a drip infusion. In another embodiment, the term "drip infusion" may refer to a gravitation infusion. In another embodiment, the term "gravitation infusion" may refer to an infusion wherein the liquid is flowing by gravity. In another embodiment, the term "infusion" may refer to a non-pumped infusion. In another embodiment, the term "infusion" may refer to a pumped infusion. In one embodiment of the invention, the term "actuate" may refer to any type of activation of another element. In another embodiment, the term "actuate" may refer to open.

In one embodiment of the invention, the term "valve" may refer to any apparatus which may be opened or closed. In another embodiment, the valve may be adapted to allow more than one flow rates.

In one embodiment, the term "infusion control valve" according to the invention, may also be referred to as a "shut-off device" or a "Smart Valve".

In one embodiment of the invention, the term "key" may refer to any apparatus which is adapted to induce opening or closing of a valve, mechanically, electrically, electromechanically, magnetically, electromagnetically or by any other appropriate way.

In one embodiment of the invention, the term "infusion valve actuator" may also be referred to as an infusion activation device or a "Smart Activator".

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What we claim is:

1. An infusion control valve functionally connected to an authentication unit; wherein said infusion control valve is normally closed thereby preventing an infusion liquid from reaching a patient; and wherein said authentication unit is configured to trigger opening of said valve when said authentication unit identifies a match between said patient and said infusion liquid, thereby initiating flow of said infusion liquid to the patient, wherein said infusion control valve is positioned above or below a drip chamber of an infusion line.

2. The valve of claim 1, wherein said authentication unit is configured to remotely trigger the opening of said infusion control valve.

3. The valve of claim 2, wherein remotely triggering comprises utilizing IR, RF, ultrasound or any combination thereof.

4. The valve of claim 1, wherein said valve comprises a key cylinder, wherein said key cylinder is adapted to allow the flow of the infusion liquid upon being actuated by the rotation of a key within said key cylinder.

5. The valve of claim 1, wherein said authentication unit comprises a patient details acquisition unit, a liquid characteristics acquisition unit, a comparison unit, adapted to match the patient details to the liquid characteristics.

6. The valve of claim 5, wherein said authentication unit is configured to identify the match between the patient and the infusion liquid by calculating a correlation value between said patient details and said liquid characteristics and to compare said correlation value to a predetermined threshold value.

7. The valve of claim 1, wherein said valve is adapted to be actuated by a valve actuator by mechanical, electrical, electromechanical, magnetic means or any combination thereof.

8. The valve of claim 1, wherein said valve is disposable.

9. The valve of claim 1, wherein said valve is reusable.

10. The valve of claim 1, wherein said valve is located outside the liquid path.

11. The valve of claim 1, wherein said valve is located within the liquid path.

12. The valve of claim 1, wherein said valve is designed to inhibit the flow of infusion liquid during replacement of an infusion container.

13. The valve of claim 1, wherein said valve is positioned between said drip chamber and a spike but not conjugated to any of them.

14. A method for delivering an infusion liquid to a patient, the method comprising utilizing an authentication unit to identify a match between the patient and the infusion liquid and triggering opening of an infusion control valve if a match is identified, thereby initiating flow of the infusion liquid to the patient wherein said infusion control valve is positioned above or below a drip chamber of an infusion line.

15. The method of claim 14, wherein triggering opening of said infusion control valve is done remotely.

16. The method of claim 15, wherein remotely triggering comprises using IR, RF, ultrasound or any combination thereof.

17. The method of claim 14, wherein said delivering comprises intravenous administration.

18. The method of claim 14, wherein said delivering comprises parenteral, epidural, intrathecal administration or any combination thereof.

19. The method of claim 14, wherein said infusion comprises saline, a drug, a pharmaceutical composition, blood, a blood product, a blood component, plasma, a plasma derivative, a biological substance, total parenteral nutrition (TPN) or any combination thereof.

20. The method of claim 19, wherein said drug comprises a chemotherapeutic agent, antibiotics, anesthetics or any combination thereof.

21. The method of claim 14, wherein triggering opening of said infusion control valve comprises utilizing a valve actuator adapted to actuate said valve by mechanical, electrical, electromechanical, magnetic means or any combination thereof.

22. The method of claim 21, wherein said valve comprises a key cylinder.

23. The method of claim 22, wherein said key cylinder is adapted to allow the flow of the infusion liquid upon being actuated by the rotation of a key within said key cylinder.

24. The method of claim 14, wherein identifying a match between the patient and the infusion liquid comprises comparing patient details to characteristics of the infusion liquid.

25. The method of claim 24, wherein comparing the patient details to the characteristics of the infusion liquid comprises calculating a correlation value and comparing the correlation value to a predetermined threshold value.

26. An infusion control system comprising an infusion control valve and valve an authentication unit; wherein said infusion control valve is normally closed thereby preventing an infusion liquid from reaching a patient; and wherein said authentication unit is configured to trigger opening of said valve when identifying a match between said patient and said infusion liquid, thereby initiating flow of said infusion liquid to the patient, wherein said infusion control valve is positioned above or below a drip chamber of an infusion line.

27. The infusion control system of claim 26, wherein said authentication unit is adapted to actuate said valve remotely.

28. The infusion control system of claim 27, wherein remotely triggered comprises means of IR, RF, ultrasound or any combination thereof.

29. The infusion control system of claim 26, wherein said authentication unit is configured to trigger opening of said infusion control valve by actuating a valve actuator configured to actuate the opening of the infusion control valve by mechanical, electrical, electromechanical, magnetic means or any combination thereof.

30. The infusion control system of claim 26, wherein said infusion control valve comprises a key cylinder.

31. The infusion control system of claim 30, wherein said key cylinder is adapted to allow the flow of the infusion liquid upon being actuated by the rotation of a key within said key cylinder.

32. The infusion control system of claim 26, wherein said authentication unit comprises a patient details acquisition unit, a liquid characteristics acquisition unit, a comparison unit, and wherein identifying the match between said patient and said infusion liquid comprises, utilizing said comparison unit to calculate a correlation value between patient details stored in said patient acquisition unit and liquid characteristics identified by said patient acquisition unit.

* * * * *